United States Patent [19]

Sellergren et al.

[11] Patent Number: 4,960,762

[45] Date of Patent: Oct. 2, 1990

[54] CHIRAL TWO-PHASE SYSTEM AND METHOD FOR RESOLUTION OF RACEMIC MIXTURES AND SEPARATION OF DIASTEREOMERS

[76] Inventors: Börje Sellergren; Björn A. Ekberg; Per-Åke Albertsson; Klaus Mosbach, all of Avd. for Tillampad Biokemi, Kemicentrum, Box 124, S-221 00 Lund, Sweden

[21] Appl. No.: 30,855

[22] PCT Filed: Jun. 27, 1986

[86] PCT No.: PCT/SE86/00315

§ 371 Date: Mar. 11, 1987

§ 102(e) Date: Mar. 11, 1987

[87] PCT Pub. No.: WO87/00165

PCT Pub. Date: Jan. 15, 1987

[30] Foreign Application Priority Data

Jun. 28, 1985 [SE] Sweden ............................. 8503220

[51] Int. Cl.$^5$ ............................................. C07B 57/00
[52] U.S. Cl. ........................................ 514/57; 514/58; 514/2; 536/125; 536/127; 536/112; 536/56; 560/78; 210/639; 210/656; 210/659
[58] Field of Search ............... 536/125, 127, 56, 112; 514/58, 257, ; 560/78; 210/635, 656, 659

[56] References Cited

OTHER PUBLICATIONS

Title Page of Journal of Chromatography, vol. 333, Pub. Date-9/27/85.
P.-A. Ablertsson, "Partition of Cell Particles and Macromolecules", Wiley, New York, 1971.
Backman, L., "Protein-Protein Interactions Studied by Counter-Current Distribution", *J. Chrom.*, vol. 196 (1980), pp. 207-216.
Albertsson, P.-A. et al., "Phase Partition—A Method for Purification and Analysis of Cell Organelles and Membrane Vesicles", *Methods of Biochemical Analysis*, vol. 28 (1982), pp. 115-150.
Takeuchi, T. et al., "Enantioselective Solvent Extraction of Neutral DL-Amino Acids in Two-Phase Systems Containing N-n-Alkyl-L-proline Derivatives and Copper(II) Ions", *Anal. Chem.*, vol. 56 (1984), pp. 1152-1155.
Allenmark, S., "Recent Advances in Methods of Direct Optical Resolution", *J. Biochem. Biophys. Meth.*, vol. 9 (1984), pp. 1-25.
Ekberg, B. et al., "Direct Chiral Resolution in an Aqueous Two-Phase system Using the Counter-Current Distribution Principle", J. Chrom., vol. 333 (1985), pp. 211-214.

*Primary Examiner*—Ronald W. Griffin
*Attorney, Agent, or Firm*—Merchant, Gould, Smith, Edell, Welter & Schmidt

[57] ABSTRACT

A chiral two-phase system for resolution of racemic mixtures, or for separation of diastereomers, is disclosed. The system comprises two immiscible liquid phases and one or more enantioselectively binding chiral components, each of which is substantially in one of said phases.

Also disclosed is a method for chiral resolution of racemic mixtures, or for separation of diastereomers. Use is here made of the fact that different enantiomers are partitioned differently between the phases in the above-mentioned two-phase system in that one of the enantiomers is selectively bound to one of the chiral components which is substantially in one of said phases.

14 Claims, 4 Drawing Sheets

CHIRAL TWO-PHASE SYSTEM AND METHOD FOR RESOLUTION OF RACEMIC MIXTURES AND SEPARATION OF DIASTEREOMERS

The invention relates to a system and a method for chiral resolution of racemic mixtures and for separation of diastereomers.

The pharmaceutical industry generally makes great demands on the optical purity of the pharmaceutical preparations. However, the synthesis of the drug frequently results in a relatively low optical purity, and the resulting product must be enriched by the right enantiomer by some method of separation.

An attractive method in the context is the direct chiral resolution based on HPLC technique (see for example reference 1). However, because of the low capacity of these systems, the use is restricted to the analytical scale, and therefore there is need in the art for a system which is suitable for upscaling and can be used for preparative purposes.

The invention aims at providing a chiral two-phase system for resolution of racemic mixtures, or for separation of diastereomers, said system being characterised in that it comprises two immiscible liquid phases and one or more enantioselectively binding chiral components, each of which is substantially in one of said phases.

Furthermore, the invention aims at providing a method for chiral resolution of racemic mixtures, or for separation of diastereomers, said method being characterised in that the different enantiomers or diastereomers are partitioned differently between the phases of a chiral two-phase system comprising two immiscible liquid phases and one or more enantioselectively binding chiral components, each of which is substantially in one of said phases, by selectively binding one of said enantiomers or diastereomers to one of the chiral components.

The two-phase system according to the invention thus is a liquid/liquid/two-phase system for direct chiral resolution. The phase system consists of two immiscible liquid phases which may consist either of two immiscible solvents or of two different polymers mixed with water. Examples of immiscible solvents are water and butanol. Examples of different polymers which in mixture with water provide two immiscible phases are a polysaccharide (such as dextran, Aquaphase) and a polyalcohol (polyethylene glycol=PEG).

Phase systems of this type are capable of resolving chiral components, such as proteins, carbohydrates, crownethers and amino acids, or derivatives thereof. By selecting suitable conditions in the two-phase system, such a chiral component can be placed to almost 100% in one phase, whereas other components partition themselves more equally between the two phases.

By selecting the chiral component such that it selectively binds one enantiomer in a racemic mixture or one component in a mixture of diastereomers, this enantiomer will lie substantially within one phase.

After that, the two phases may be separated either by extraction or by means of a multistage process, such as countercurrent distribution.

Examples of carbohydrates that may be used as chiral components in the system according to the invention are cyclodextrin and cellulose. As chiral amino acids, use may be made of D- and/or L-proline, and in that case one phase may contain a D-proline derivative and the other phase a L-proline derivative.

The invention will now be described in more detail, reference being had to the following nonrestrictive Examples.

EXAMPLE 1

The protein BSA (bovine serum albumin) is used as chiral component for separation of D,L-tryptophan. The protein was located in the bottom phase of a PEG/dextran system.

Chemicals and phase system

Dextran 40 was obtained from Pharmacia (Uppsala, Sweden), and polyethylene glycol PEG 6000 (now renamed PEG 8000) from Union Carbide (N.Y., USA). The composition of the phase system was: 10% (w/w) Dextran 40, 7% (w/w) PEG 6000, 0.1 M sodium chloride and 50 mM sodium carbonate buffer (pH 9.2). Bovine serum albumin (6.5 g) (Sigma, No. A-3912, fraction V) was added per 100 g phase system. The albumin-containing phase system was shaken carefully and then left overnight in cold store (4° C.). D- and L-tryptophan had been obtained from Sigma and L-(side chain-2,3-$^3$H)-tryptophan, specific activity: 50 $\mu$Ci per nmol, from Amersham International (U.K.).

Countercurrent distribution

An automatic countercurrent distribution equipment with 60 cavities was used (5, 6). To cavities Nos. 1–59, 0.79 ml of respectively top and bottom phase was added, and cavity No. 0 was filled with 0.79 ml bottom phase and the sample is (9 $\mu$mol of each enantiomer of tryptophan) dissolved in 0.79 ml top phase. The shaking time was 40 s, and the partition time 12 min. After 60 transfers (4° C.) the contents of the cavities were collected in a fraction collector. The top phase of every third fraction was diluted to give a suitable absorbance at 280 nm. The radioactivity both in the top phase and in the total system was measured in a beta-scintillation counter. The scintillation liquid was Lumagel (Lumac, 6372 AD Schaesberg, The Netherlands).

Measuring the binding of L-tryptophan to serum albumin

In fractions Nos. 0–5 the radioactivity of the top phase and of the total phase system was measured, and the difference therebetween gave the radioactivity of the bottom phase. From the partition coefficient of L-tryptophan, the amount of free L-tryptophan in the bottom phase was calculated. Since the total radioactivity of the bottom phase was known, the amount of L-tryptophan bound to serum albumin could be calculated (for further details, see FIG. 2 in reference 7).

Results and discussion

The partition of serum albumin depends on, inter alia, the molecular weight of the polymers and the ion content. Here, a phase system was sought in which serum albumin has a low partition coefficient, and this is made possible with dextran of low molecular weight (8) and sodium chloride as the dominating salt. In this system, 95% of the serum albumin were in the bottom phase, and the free tryptophan partitioned more equally between the phases (partition coefficient: 1.2).

When the enantiomers were applied separately in the countercurrent distribution, the profiles according to FIG. 1 were obtained. The enantioselectivity is obvious: the L-enantiomer was retained more in the bottom phase than the D-enantiomer ($G_L=0.13, G_D=0.39$). A separation factor ($G_D/G_L$) of 3.1 was obtained. It should therefore be possible to obtain several optically pure fractions.

Similar results were obtained on application of the racemic mixture (FIG. 2). No resolution of the racemate was obtained when separation was carried out without serum albumin. A minor proportion of tritium-labelled L-tryptophan was added, and the major proportion resulted in a peak in the same location as the unlabelled L-form according to FIG. 1. However, part of the tritium labelling was found in fractions Nos. 20–40, presumably because of labelled impurities (degradation products) in the tritium-labelled L-tryptophan which was employed and which was 2 years old.

By determining the partition of the tritium-labelled L-tryptophan in fractions Nos. 0–5, the concentration of free and bound L-tryptophan in the bottom phase, containing serum albumin, could be calculated. A Scatchard plot of these data is shown in FIG. 3. An association constant of $2.9 \cdot 10^4 M^{-1}$ was obtained, which is well in agreement with published values obtained by other methods (2, 9–12). The number of binding sites was 0.4 (i.e. less than 1), which is to be expected according to other studies (2, 10–12). The low number of binding sites in some studies may be due to the fact that fatty acids are present in the BSA preparation. Since the serum albumin in this study was practically free from fatty acids, a more likely explanation is an inhibition by the phase system polymers. Polyethylene glycol resembles decanol which has been found to reduce the binding of tryptophan to bovine serum albumin (2).

EXAMPLE 2

As chiral component, use is made of cellulose in solid form which was located in the bottom phase of a dextran-PEG-phase system and used for separation of D,L-tryptophan.

Chemical and phase system

Dextran 40 (Pharmacia) and Poly(ethylene glycol) PEG 8000 (Union Carbide, N.Y.). The composition of the phase system was: 10% (w/w) Dextran, 7% (w/w) PEG, 0.5% (w/w) Imidazole and 0.1 M sodium citrate, pH 8.0. 7.5 g cellulose were added per 100 g phase system. The phase system was shaken carefully and then left overnight in cold store (4 C.). D- and L-tryptophan had been obtained from Sigma.

Countercurrent distribution

A 60-cavity automatic countercurrent distribution equipment was used (5). To cavities Nos. 1–59, 0.79 ml of respectively top and bottom phase was added. Cavity No. 0 was filled with 0.79 ml bottom phase and the sample (0.40 μmol of each enantiomer) dissolved in 0.79 ml top phase. Shaking was conducted for 40 s, and the partition time was 20 min. After 60 transfers in cold store, the contents of each cavity were collected in 60 test tubes.

Analysis and results

The absorbance at 280 nm on every other top phase was measured directly (FIG. 4).

EXAMPLE 3

As chiral component, use was made of the protein BSA (bovine serum albumin) in an Aquaphase-PEG-phase system for separation of R,S-methylsulfinyl benzoic acid on a semipreparative scale.

Chemicals and phase system

Aquaphase (Perstorp) and Poly(ethylene glycol)-PEG 8000 (Union Carbide, New York). The composition of the phase system was: 14% (w/w) Aquaphase, 5% (w/w) PEG, 40 mM NaCl and 20 mM sodium phosphate, pH 5.3. 7.0 g bovine serum albumin (Sigma) were added per 100 g phase system. The phase system was shaken carefully and then left overnight in cold store (4° C.).

Countercurrent distribution

Use was made of an automatic countercurrent distribution equipment comprising 60 cavities (5). To cavities Nos. 1–59, 0.79 ml of respectively top and bottom phase was added. The cavity No. 0 was filled with 0.79 ml bottom phase and the sample (R,S-methylsulfinyl benzoic acid, 17 mg, 92 μmol) dissolved in 0.79 ml top phase. Shaking was conducted for 40 s, and the partition time was 20 min. After 60 transfers in cold store, the contents of each cavity were collected in 60 test tubes.

Analysis and results

Part of the top phase in every other tube was diluted to a suitable absorbance 225 nm (FIG. 5). 0.3 ml of the top phase of fractions Nos. 10–13 was combined and diluted with part of 40 mM NaCl, 20 mM sodium phosphate, pH 5.3, whereupon the optical rotation was measured in a Perkin-Elmer 141 polarimeter. Fractions Nos. 14–17, 18–20, 21–24, 25–27, 28–30 and 31–33 were combined, diluted and measured in the same manner. The results are shown in Table 1.

TABLE 1

|  | 22 α D |
| --- | --- |
| Fractions Nos. 10–13 | 4.30° C. |
| Fractions Nos. 14–7 | 3.80° C. |
| Fractions Nos. 18–20 | 3.85° C. |
| Fractions Nos. 21–24 | 4.48° C. |
| Fractions Nos. 25–27 | 4.02° C. |
| Fractions Nos. 28–30 | 4.19° C. |
| Fractions Nos. 31–33 | 4.22° C. |

EXAMPLE 4

As chiral component, use was made of beta-cyclodextrin coupled to Aquaphase (Perstorp) which was partitioned in an Aquaphase/PEG-phase system for separation of R,S-terbutaline.

Chemicals and phase system

Aquaphase (Perstorp), Poly(ethylene glycol)PEG 8000 (Union Carbide, N.Y.), p-toluene sulfonyl chloride (Sigma), 1,4-diamino butane (Janssen, Belgium), β-cyclodextrin (Stadex AB, Sweden).

Synthesis of p-toluene sulfonyl-β-cyclodextrin(β-CD-OTs)

25 g (22 mmol) β-cyclodextrin (washed with diethyl ether and dried over $P_2O_5$) are dissolved in 100 ml dry pyridine, the solution is saturated with $N_2$ and placed in an ice bath. 4.18 g (22 mmol) p-toluenesulfonyl chloride are dissolved in 20 ml dry pyridine, the solution is saturated with $N_2$ and placed in an ice bath. The two solutions are mixed and caused to react at room temperature overnight. The solution is evaporated, and the resulting tough oil is recrystallised from distilled water. The product is dried over $P_2O_5$. Yield 25.9 g. Elementary analysis gave C: 36.9–37.1%, H: 5.36–5.37%, N: 1.06–1.08%, S: 0.38%. Thus, the product contains 6.95% (w/w) pyridine, and about every sixth β-cyclodextrin unit is tosylated. $R_f$ 0.80 (Silicaplatten, Merck in $CHCl_3$-MeOH 9-1).

Synthesis of p-toluene sulfonyl-Aquaphase(Aqph-OTs)

10 g (61 mmol) Aquaphase (dried over $P_2O_5$) are slurried in 75 ml dry pyridine, the mixture is saturated with $N_2$ and placed in an ice bath. 22 g (116 mmol) p-toluenesulfonyl chloride are dissolved in 75 ml dry pyridine, the solution is saturated with $N_2$ and placed in an ice bath. The components are mixed, and the mixture is slowly agitated at room temperature for 3 days. A minor undissolved residue remains which is filtered off, whereupon the solution is evaporated. The resulting semicrystalline mass is treated with 500 ml 0.5 M sodium phosphate buffer, pH 7, for some hours, whereupon the product is obtained. The substance is washed carefully with distilled water and then dried over $P_2O_5$. Yield 16 g. Elementary analysis gave C: 28.2–28.5%, H: 2.81–2.88%, N: 0.70–0.72%, S: 6.01–6.16%. (Elementary analysis of Aquaphase gave C: 42.6–42.8%, H: 6.60–6.65.) The product thus contains 4.61% (w/w) pyridine, and every other carbohydrate monomer is tosylated. $R_f$ 0.00–0.10, no traces of p-toluenesulfonyl chloride (Silicaplatten, Merck in $CHCl_3$-MeOH 9-1 and $CHCl_3$-MeOH-HOAc-$H_2O$ 6-4-1-1).

Synthesis of 1,4-diamino-butane -Aquaphase($H_2N$-$(CH_2)_4$-NH-Aqph)

15 g (60 mmol) Aqph-OTs (above) are added in batches to 60 ml 1,4-diamino butane. After the addition, the solution is heated to 80° C. for 4 hours and is then left overnight at room temperature. The solution is evaporated, the remainder is diluted with 150 ml distilled water, and pH is adjusted to 7 with 6 M HCl. The neutralised solution is dialysed against 3×20 l distilled water. Freeze drying gave 2.6 g product. Elementary analysis gave C: 43.2–43.3%, H: 6.85–6.97%, N: 7.28–7.59%. Thus, every other carbohydrate monomer has been provided with an amino spacer. $R_f$ 0.00–0.10 (Silicaplatten, Merck in $CHCl_3$-MeOH 9-1 and $CHCl_3$-MeOH-HOAc-$H_2O$ 6-4-1-1), no traces of 1,4-diamino butane.

Synthesis of β-CD- NH-$(CH_2)_4$ -NH-Aqph 2,6 g (13 mmol) $H_2N$-$(CH_2)_4$-NH-Aqph (above) are dissolved together with 15 g (actually 12 mmol tosylated β-cyclo dextrin) β-CD-OTs (above) containing 11 mmol pyridine and 95 ml DMF. After agitation at room temperature overnight, 0.8 ml triethyl amine is added. Coupling is allowed to continue for 6 days at room temperature, and finally heating is effected to 80° C. during 4 hours. The solution is evaporated, and the remainder is diluted with 50 ml distilled water, pH is adjusted with 1 M HCl to 7. The solution is dialysed against 3×20 l distilled water. Freeze drying gave 3.9 g product. Elementary analysis gave C: 42.3–42.6%, H: 6.26–6.27%, N: 2.24–2.32%. Thus, at least every third carbohydrate monomer has been provided with a β-cyclodextrin unit (actually 0.4 mol β-cyclodextrin units/mol carbohydrate monomer). $R_f$ 0.00–0.10 (Silicaplatten, Merck in $CHCl_3$-MeOH 9-1 and $CHCl_3$-MeOH-HOAc-$H_2O$ 6-4-1-1), ninhydrin positive reaction left. Composition of the phase system: 14% (w/w) Aquaphase, 2.5% (w/w) β-CD-NH-$(CH_2)$ 4-NH-Aqph, 5% PEG, 0.1 M $Li_2SO_4$, 6.25 mM sodium citrate, pH 6.0. The phase system was shaken carefully and left overnight in cold store (4° C.).

Countercurrent distribution

Use was made of an automatic countercurrent distribution equipment with 60 cavities (5). To cavities Nos. 1–59, 0.79 ml of respectively bottom and top phase was added, cavity No. 0 was filled with 0.79 ml bottom phase and the sample (4.5 μmol R,S-terbutaline) dissolved in 0.79 ml top phase. Shaking was conducted for 40 s, and the distribution time was 20 min. After 60 transfers in cold store, the contents of the respective cavities were collected in 60 test tubes.

Analysis and results

The absorbance at 280 nm on the top phase of every third fraction was measured (FIG. 6).

EXAMPLE 5

As chiral component, use was made of L-proline (Pro) coupled to Aquaphase (Perstorp) which was partitioned in an Aquaphase/PEG-phase system and used for separation of D,L-tryptophan.

Chemicals and phase system

Aquaphase (Perstorp), Polyethylene glycol PEG 8000 (Union Carbide, N.Y.), p-toluene sulfonyl chloride (Sigma), Proline (Sigma). Composition of the phase system: 5% (w/w) Aquaphase-Pro, 10% (w/w) Aquaphase, 5% (w/w) PEG 8000, 0.1 M NaCl.

Synthesis of p-toluene sulfonyl-Aquaphase (Aqph-OTs)

10 g (61 mmol) Aquaphase (dried over $P_2O_5$) is slurried in 75 ml dry pyridine, the mixture is saturated with $N_2$ and placed in an ice bath. 22 g (116 mmol) p-toluene sulfonyl chloride are dissolved in 75 ml dry pyridine, the solution is saturated with $N_2$ and placed in an ice bath. The components are mixed, and the mixture is agitated slowly at room temperature for 3 days. A minor undissolved residue remains which is filtered off, and the solution is evaporated. The resulting semicrystalline mass is treated with 500 ml 0.5 M sodium phosphate buffer, pH 7, for several hours during which the product is obtained. The substance is washed carefully with distilled water and then dried over $P_2O_5$. Yield 16 g. Elementary analysis gave C: 28.2–28.5%, H: 2.81–2.88%, N: 0.70–0.72%, S: 6.01–6.16%. Elementary analysis of Aquaphase gave C: 42.6–42.8%, H: 6.60–6.65%). Thus, the product contains 4.61% (w/w) pyridine. Every other carbohydrate monomer is tosylated. $R_f$ 0.00–0.10, no traces of p-toluene sulfonyl chloride (Silicaplatten, Merck in $CHCl_3$-MeOH 9-1 and $CHCl_3$-MeOH-HOAc-$H_2O$ 6-4-1-1).

Synthesis of Aquaphase-Pro 10 g (40 mmol) Aqph-OTs and 7 g (60 mmol) L-proline are slurried in 100 ml DMF under nitrogen gas. 6 g triethyl amine are added, and the mixture is heated to 80° C. for 10 hours, whereupon it is left overnight at room temperature. After filtration and evaporation, the substance is dissolved in 150 ml water and neutralised, followed by freeze drying. The product is dried over $P_2O_5$. $R_f$ 0.4 (Silicaplatten, Merck in $CHCl_3$-HOAc-$H_2O$: 6-4-1-1). Positive ninhydrin reaction.

Countercurrent distribution

Use was made of an automatic countercurrent distribution equipment having 60 cavities (5). To cavities Nos. 1-59, 0.79 ml of respectively bottom and top phase was added, cavity No. 0 was filled with 0.79 ml bottom phase and the sample (5 mg D,L-tryptophan) dissolved in 0.79 ml top phase. Shaking was conducted for 40 s, and the distribution time was 20 min. After 60 transfers in cold store, the respective cavity contents were collected in 60 test tubes.

Analysis and results

The absorbance at 280 nm on the top phase of every third fraction was measured (FIG. 7).

EXAMPLE 6

In modification of Example 5, D-proline coupled to PEG was added to the PEG phase. Thus, L-proline-Aquaphase is in the bottom phase, and D-proline-PEG in the top phase. Due to opposed selectivity, there is thus obtained a more efficient separation if Example 5 is followed in other respects. D-proline-PEG is simply coupled to PEG via tosyl or tresyl activation.

Our results indicate that liquid/liquid/two-phase systems may be used for direct chiral resolution of racemic mixtures if an enantioselectively binding component is included in the phase system. These systems may be used both for analytical and for preparative purposes. Since liquid/liquid distribution is readily upscaled, these phase systems are especially interesting for large scale resolution of racemic mixtures.

FIG. 1 shows countercurrent distribution of L-tryptophan (○) and D-tryptophan (●) applied separately (9 μmol.). The absorbance in the top phase of every third fraction was measured at 280 nm.

FIG. 2 shows countercurrent distribution of racemic L,D-tryptophan (18 μmol), with traces of ($^3$H)-L-tryptophan. The absorbance in the top phase of every third tube was measured at 280 nm. To another set of every third tube, 1.0 ml distilled water was added to give a one-phase system from which samples were taken for estimation of ($^3$H)-L-tryptophan content. Radioactivity is given in percent of total amount of radioactivity added.

REFERENCES

Figure 1:
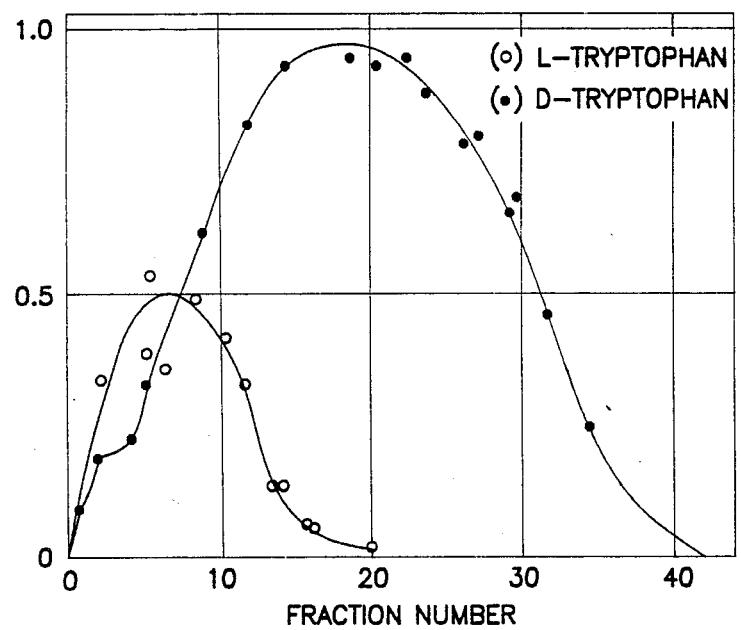
Figure 2:
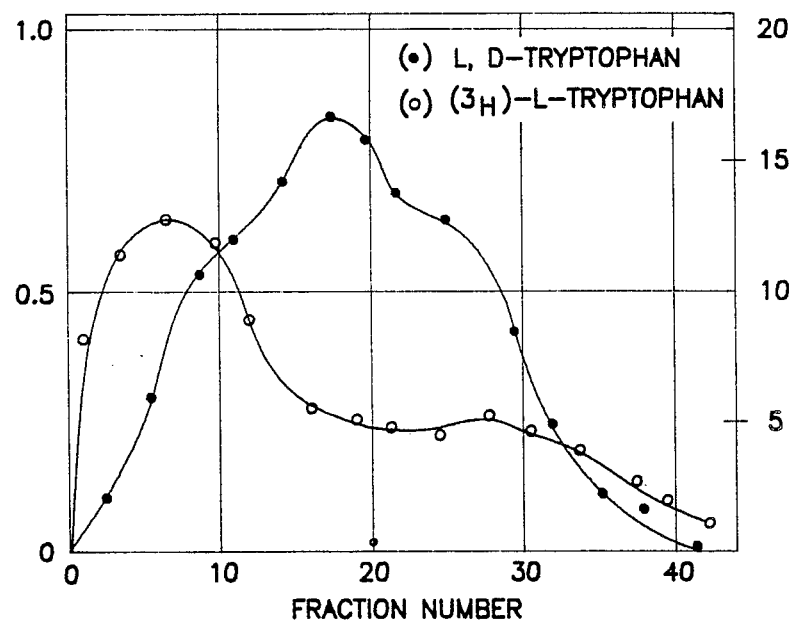
Figure 3:
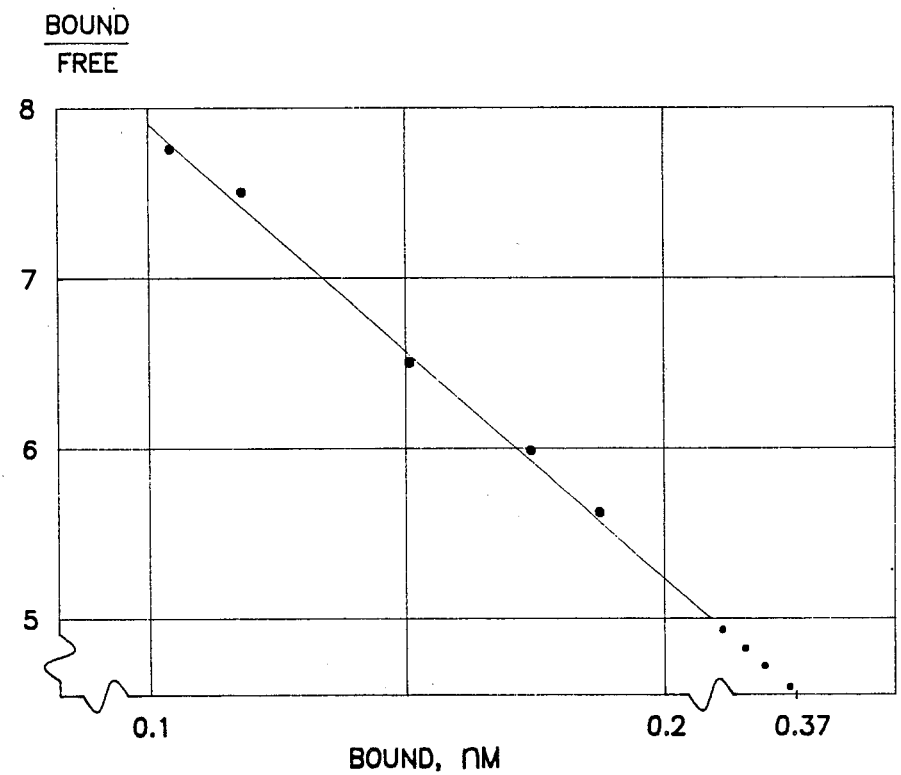
FIG. 3 is Scatchard plot of binding between L-tryptophan and bovine serum albumin, calculated on values from tubes Nos. 0–5.
Figure 4:
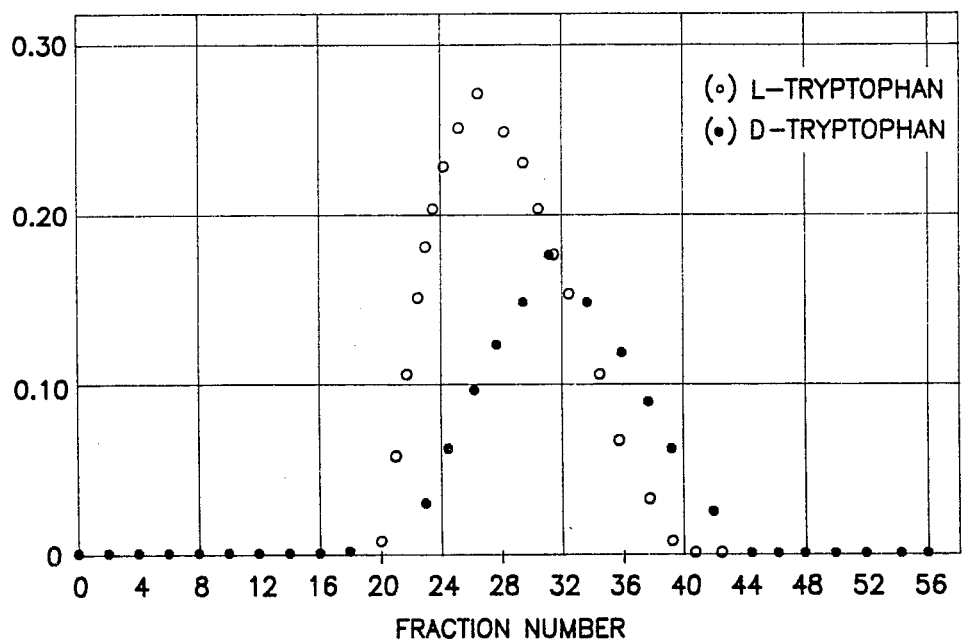
FIG. 4 shows countercurrent distribution of L-tryptophan (○) and D-tryptophan (○) applied separately in the equipment. Separation factor ($G_D/G_L$) 1.23.
Figure 5:
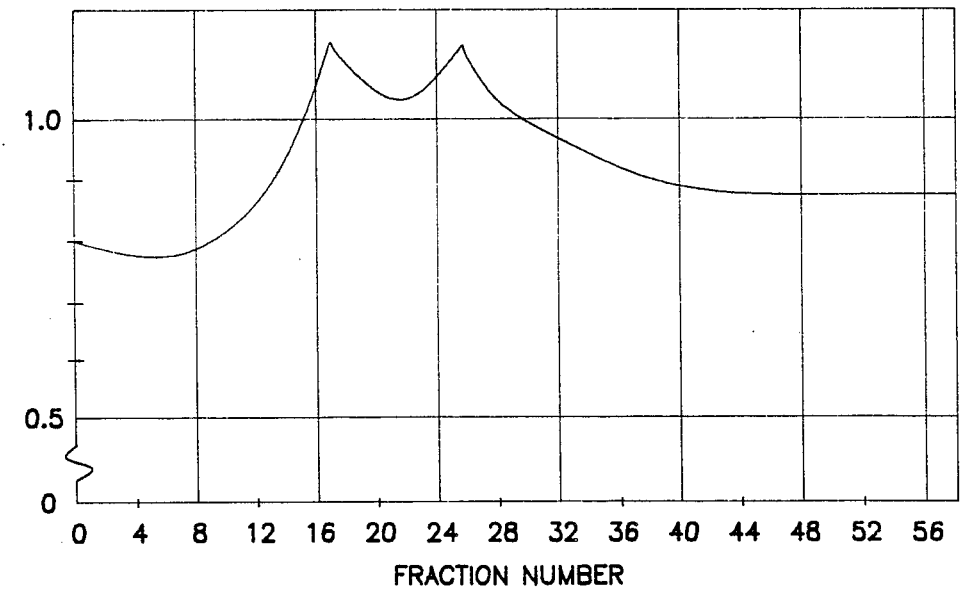
FIG. 5 shows countercurrent distribution of R,S-methylsulfinyl benzoic acid. Separation factor 1.56.
Figure 6:
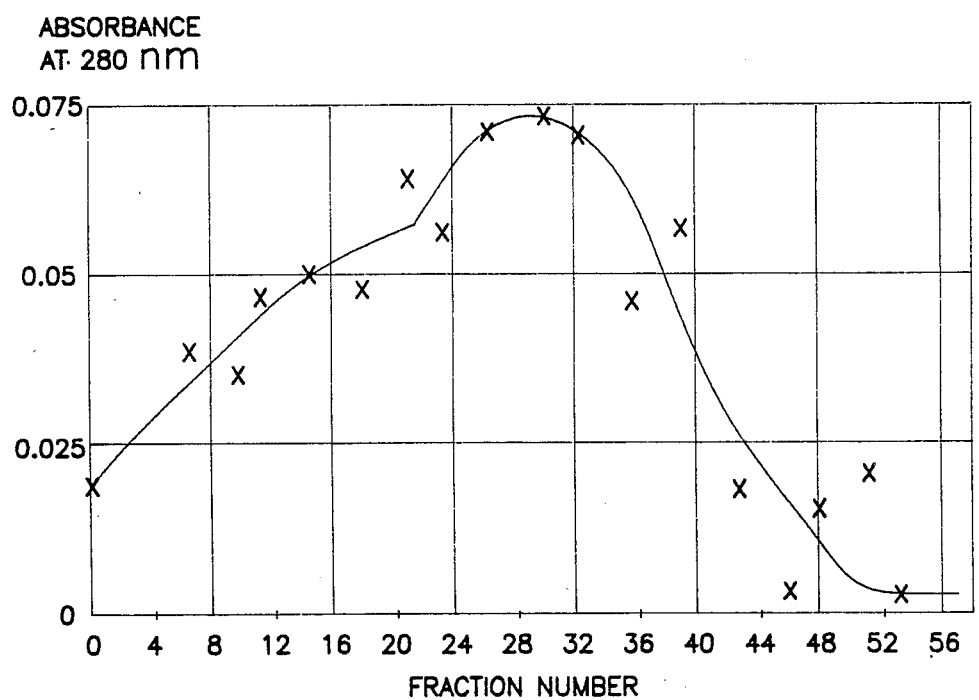
FIG. 6 shows countercurrent distribution of R,S-tetrabutaline (R,S-[3,5-dihydroxyphenyl]-2-[tert(-butylamino]ethanol).
Figure 7:
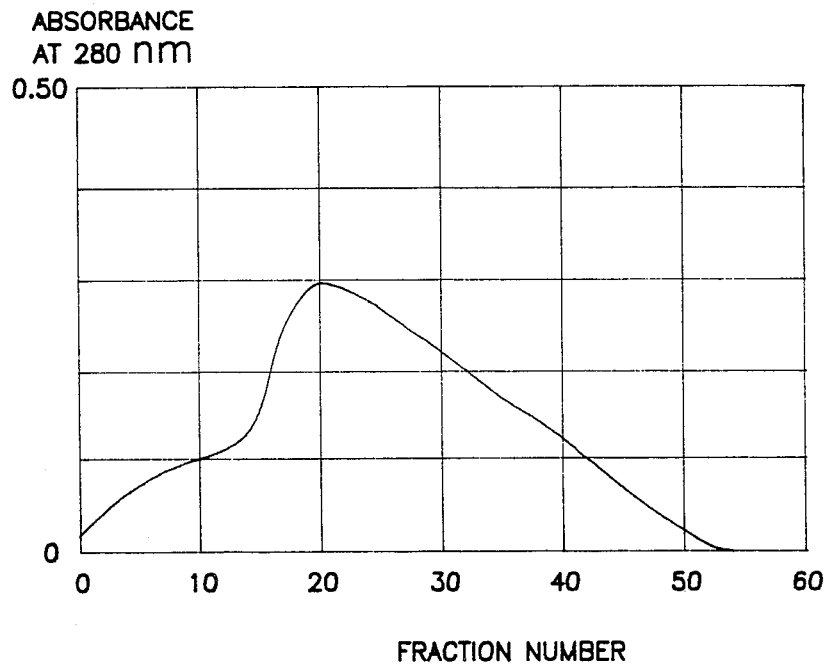
FIG. 7 shows countercurrent distribution of D,L-tryptophan in a Pro-Aquaphase/Aquaphase/PEG system.

1. S. Allenmark, J. Biochem. Biophys. Meth., 9 (1984) 1–25.
2. P.-Å. Albertsson, Partition of Cell Particles and Macromolecules, Wiley, N.Y., 1971.
3. P.-Å. Albertsson, B. Andersson, C. Larsson and H.-E. Åkerlund, Meth. Biochem. Anal., 28 (1982) 115–150.
4. P.-Å. Albertsson, Meth. Biochem. Anal., 29 (1983) 1–24.
5. V.P. Shanbhag, R. Södergå, H. Carstensen and P.-Å. Albertsson, J. Ster. Biochem., 4 (1973) 537.
6. L. Backman, J. Chromatogr., 196 (1980) 207–216.
7. G.F. Fairclough, Jr and J.S. Fruton, Biochemistry, 5 (1966) 673–683.
8. T.P. King and M. Spencer, J. Biol. Chem., 245 (1970) 6134–6148.
9. V.J. Cunningham, L. Hay and H.B. Stoner, Biochem., J., 146 (1975) 653–658.

We claim:

1. A method for chiral resolution of racemic mixtures, or for separation of diastereomers, wherein the different enantiomers or diastereomers are partitioned differently between the phases of a chiral two-phase system comprising two immiscible liquid phases and one or more enantioselectively binding chiral components, each of which is substantially in one of said phases, by selectively binding one of said enantiomers or diastereomers to one of the chiral components.

2. A method according to claim 1, wherein the two immiscible liquid phases comprise two different polymers.

3. A method according to claim 2, wherein one of the two immiscible liquid phases comprises a polyalcohol and the other of the two immiscible liquid phases comprises a polysaccharide.

4. A method according to claim 3, wherein the polyalcohol comprises polyethylene glycol.

5. A method according to claim 3, wherein the polysaccharide comprises dextran.

6. A method according to claim 1, wherein the two immiscible liquid phases comprise two immiscible solvents.

7. A method according to claim 6, wherein one of the two immiscible solvents comprises water and the other of the two immiscible solvents comprises butanol.

8. A method according to claim 1, wherein the one or more enantioselectively binding chiral components are selected from the group consisting of protein, carbohydrate, amino acid, and derivatives thereof.

9. A method according to claim 8, wherein the protein comprises albumin.

10. A method according to claim 8, wherein the carbohydrate is selected from the group consisting of cyclodextrin, cellulose, and derivatives thereof.

11. A method according to claim 8, wherein the amino acid is selected from the group consisting of D-proline, L-proline, and derivatives thereof.

12. A method according to claim 11, wherein D-proline or a derivative thereof is substantially in one of the two immiscible liquid phases, and L-proline or a derivative thereof is substantially in the other of the two immiscible liquid phases.

13. A method according to claim 1, further comprising separating the two immiscible liquid phases by countercurrent distribution.

14. A method for chiral resolution of a mixture of a D-tryptophan enantiomer and a L-tryptophan enantiomer, wherein the enantiomers are partitioned differently between phases of a chiral two-phase system comprising:
    (a) two immiscible liquid phases, including a dextran liquid phase and a polyethylene glycol liquid phase; and
    (b) bovine serum albumin, wherein the albumin is substantially in one of the liquid phases;
by selectively binding the L-tryptophan enantiomer to the bovine serum albumin.

* * * * *